United States Patent [19]

Klemm

[11] Patent Number: Plant 6,994

[45] Date of Patent: Aug. 22, 1989

[54] GERANIUM PLANT NAMED KLEFISALL

[75] Inventor: Siegfried Klemm, Stuttgart, Fed. Rep. of Germany

[73] Assignee: Klemm & Sohn, Stuttgart, Fed. Rep. of Germany

[21] Appl. No.: 237,398

[22] Filed: Aug. 29, 1988

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Cha. W. Rummler

[57] ABSTRACT

A new geranium cultivar particularly distinguished by the large size and deep red color of its flower clusters, each containing about sixty-five flowers in loose formation which stand on stems about 15 cm. long, its profuse and continuous blooming habit, and its abundance of medium size leaves which have clearly visible dark zonation, providing a foliage body extending about 15 cm. above the soil.

1 Drawing Sheet

BACKGROUND OF THE NEW PLANT

This new pelargonium variety originated as a sport of the variety 'PAC Isabell' (unpatented) grown in my nursery at Stuttgart, West Germany, this plant having darker leaves than those of the parent so that the color of the blooms appears to be a more intensive red. This sport, discovered in 1986, was propagated through several generations by means of cuttings, under my direction at Stuttgart, which demonstrated that the unique characteristics of this plant would hold true from generation to generation and appeared to be firmly fixed. Propagation of this new plant, by cuttings, on a commercial scale is now being done at Stuttgart.

DESCRIPTION OF THE DRAWING

My new geranium cultivar is illustrated by the accompanying drawing, which shows the general characteristics of the new variety grown as a potted plant, the drawing being a photographic print with color reproduction as nearly true as it is reasonably possible to obtain by conventional commercial photographic procedures.

DESCRIPTION OF THE NEW PLANT

The following is a detailed description of this new variety of geranium plant as grown at Stuttgart, West Germany, and observed in the early Spring of 1988, with color designations according to The R.H.S. Colour Chart published by The Royal Horticultural Society of London, England.

THE PLANT

Origin: Sport.
Parent: Geranium variety 'PAC Isabell' (unpatented).
Classification:
*Botanic.—Pelargonium zonale hybrid.*
*Commercial.*—Geranium.
Form: Bush.
Height: About 17 cm.
Main stem length: About 15 cm.
Growth: Vigorous, bushy and compact with good strength.
Branching character: Normal.
Foliage:
*Quantity.*—Lush.
*Size of leaf.*—Medium.

*Leaf shape.*—Reniform with bicrenate margins.
*Texture.*—Smooth.
*Color.*—Upper side — Green with dark zonation. Under side — Green.
*Ribs and veins.*—4 to 6 main veins on each leaf.

THE BUD

Size: Normal.
*Diameter.*—About 8 mm.
*Length.*—About 14 mm.
Shape: Pointed ovoid.
Rate of opening: Medium.
Color of petals:
*When sepals first divide and when petals begin to unfurl.*—Red.
Sepals:
*Number.*—Five.
*Shape.*—Generally ovate with acuminate tip. The sepals stand up when the flowers open.
*Color.*—Green, both inside and outside.
Calyx:
*Shape.*—Flat.
*Splitting.*—The calyx does not split.
Flower stem:
*Length.*—About 16 cm.
*Aspect.*—Very slightly hairy.
*Character.*—Rigid and erect.
*Color.*—Green.

THE FLOWER

Blooming habit: Continuous from early to late throughout the growing season and, with adequate temperature and photoperiod, blooming the year around under glass.
Size: Medium.
*Cluster diameter.*—About 14.5 cm.
*Cluster depth.*—About 11 cm. between flower stems.
Borne: The flowers are borne singly on the umbel stems of a cluster.
Shape: *When bloom first opens.*—Cup-shaped. *When bloom matures.*—Flat cup.
Petalage:
*Number of petals.*—9 or 10.
*Arrangement.*—Imbricated.
*Form.*—Broad with entire margins and rounded apex.

*Texture.*—Soft.
*Aspect.*—Velvety.
*Color.*—RHS 34-A.

Petaloids:
*Number.*—Few.
*Size.*—About 3 to 5 mm.
*Color.*—Red.

Peduncle:
*Length.*—About 15 cm.
*Color.*—Green.
*Character.*—Upright with good strength.

Lasting quality:
*On plant.*—About 15 days.

REPRODUCTIVE ORGANS

Stamens:
*Number.*—Seven.
*Arrangement.*—Around the pistil.
*Anthers.*—Size: About 2 mm. Color: White.

Filaments:
*Length.*—About 4 to 5 mm.
*Color.*—White.

*Pollen.*—Color: Orange.

Pistil:
*Number.*—One.
*Style.*—Length: About 2 to 4 mm. Color: Green.
*Stigma.*—Five cells. Color: White.

Character of the ovaries: Like all Pelargonium.

THE FRUIT

Fertility: Very fertile.
Shape: Ovoid.
Color at maturity: Brown to dark brown.

This new plant most resembles the parent 'PAC Isabell'. The color of the leaves, however, is darker so that the color of the flowers appears to be more intensive red.

I claim:

1. A new geranium cultivar, substantially as herein shown and described, characterized by its abundant production of umbel-formed clusters of large florets and the red coloration of the flowers.

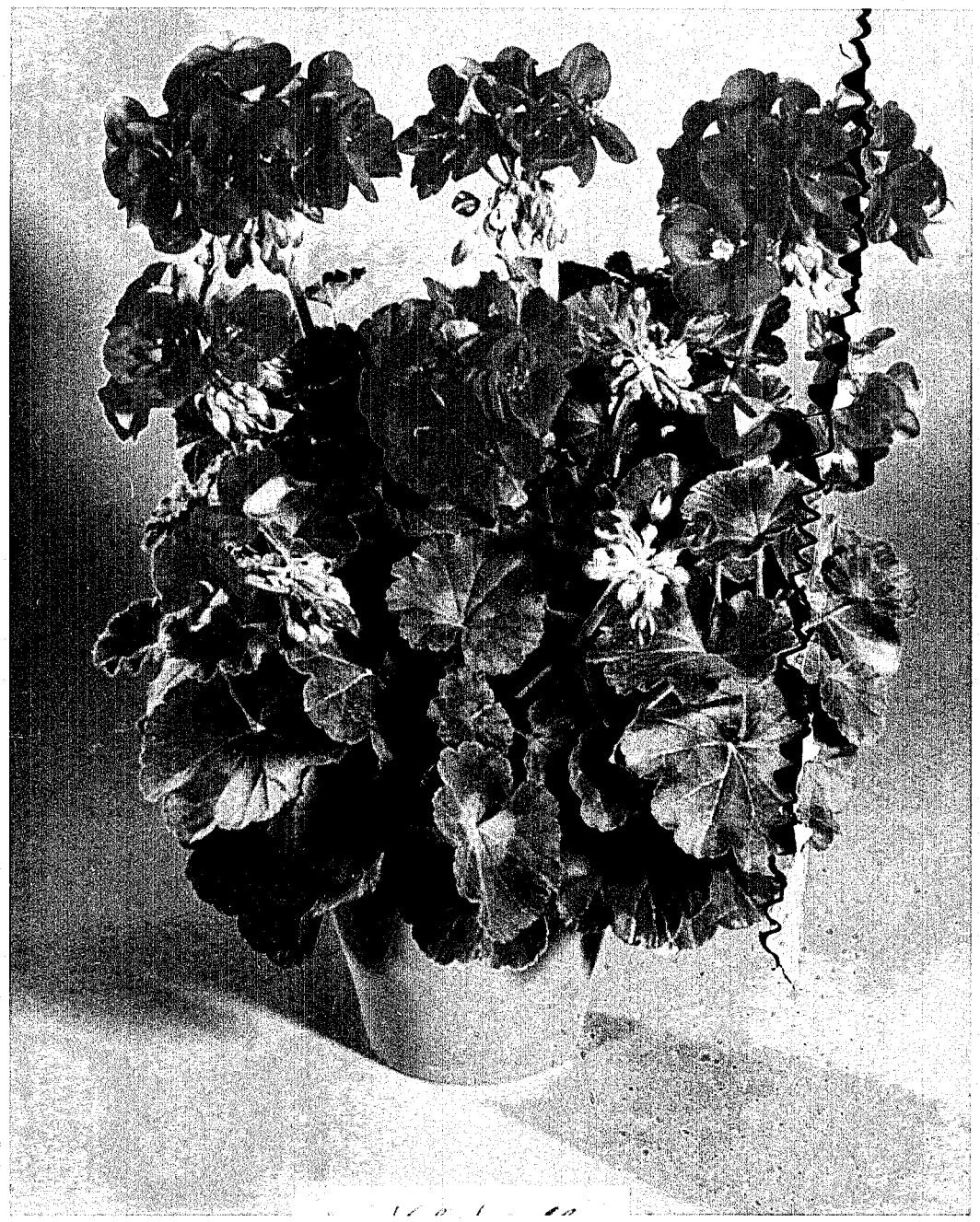

* * * * *